US008221381B2

(12) United States Patent
Muir et al.

(10) Patent No.: US 8,221,381 B2
(45) Date of Patent: Jul. 17, 2012

(54) CONTAINER SYSTEM FOR RELEASABLY STORING A SUBSTANCE

(75) Inventors: Rod Muir, South Mountain (CA); Derek Kirkland, Chelsea (CA); Ian Curry, Kanata (CA); Roy Sunstrum, Richmond (CA); Paul Lem, Ottawa (CA); H. Chaim Birnboim, Ottawa (CA)

(73) Assignee: DNA Genotek Inc., Ontario (CA)

( * ) Notice: Subject to any disclaimer, the term of this patent is extended or adjusted under 35 U.S.C. 154(b) by 669 days.

(21) Appl. No.: 12/096,767

(22) PCT Filed: Dec. 11, 2006

(86) PCT No.: PCT/CA2006/002009
§ 371 (c)(1),
(2), (4) Date: Nov. 24, 2008

(87) PCT Pub. No.: WO2007/068094
PCT Pub. Date: Jun. 21, 2007

(65) Prior Publication Data
US 2009/0216213 A1 Aug. 27, 2009

Related U.S. Application Data

(60) Provisional application No. 60/748,977, filed on Dec. 9, 2005.

(51) Int. Cl.
*A61B 19/00* (2006.01)
*A61F 5/32* (2006.01)
(52) U.S. Cl. ....................................................... 604/415
(58) Field of Classification Search .................. 604/411, 604/412, 414–416
See application file for complete search history.

(56) References Cited

U.S. PATENT DOCUMENTS

| | | | |
|---|---|---|---|
| 4,583,971 | A | 4/1986 | Bocquet et al. |
| 4,741,346 | A | 5/1988 | Wong et al. |
| 5,140,043 | A | 8/1992 | Darr et al. |
| 5,364,763 | A | 11/1994 | Kacian |
| 5,496,562 | A | 3/1996 | Burgoyne |
| 5,567,309 | A | 10/1996 | Classon et al. |
| 5,807,527 | A | 9/1998 | Burgoyne |
| 5,817,630 | A | 10/1998 | Hofmann et al. |
| 5,980,834 | A | 11/1999 | Bruno |

(Continued)

FOREIGN PATENT DOCUMENTS

CA 2072331 12/1992
(Continued)

OTHER PUBLICATIONS http://www.simport.com/products/tubes-caps-and-vials/tubes/t501. html, Copyright 2009-2011.*

(Continued)

*Primary Examiner* — Melanie Hand
(74) *Attorney, Agent, or Firm* — Clark & Elbing LLP; Kristina Bieker-Brady

(57) ABSTRACT

The present invention provides a container system for releasably storing a substance. The container system includes a vial having a sample storage chamber and a piercing member for piercing a membrane in the lid, which membrane seals a substance within a reservoir in the lid until the membrane is pierced by the piercing member. The container system optionally includes a funnel. There is also provided a method and kit for use of such a container system.

50 Claims, 15 Drawing Sheets

U.S. PATENT DOCUMENTS

| | | | |
|---|---|---|---|
| 6,138,821 | A | 10/2000 | Hsu |
| 6,176,836 | B1 | 1/2001 | Trudil et al. |
| 6,242,188 | B1 | 6/2001 | Dattagupta et al. |
| 6,291,178 | B1 | 9/2001 | Schneider |
| 6,309,827 | B1 * | 10/2001 | Goldstein et al. ............ 435/6.11 |
| 6,503,716 | B1 | 1/2003 | Lai et al. |
| 6,551,777 | B1 | 4/2003 | Shuber et al. |
| 6,582,415 | B1 * | 6/2003 | Fowles et al. ................. 604/413 |
| 6,617,170 | B2 | 9/2003 | Augello et al. |
| 6,716,392 | B1 | 4/2004 | Putcha et al. |
| 6,832,994 | B2 * | 12/2004 | Niedospial et al. ........... 604/411 |
| 6,869,769 | B2 | 3/2005 | Burgoyne |
| 7,482,116 | B2 | 1/2009 | Birnboim |
| 2001/0008614 | A1 | 7/2001 | Aronowitz |
| 2002/0026046 | A1 | 2/2002 | Pasloske et al. |
| 2002/0081575 | A1 | 6/2002 | Small et al. |
| 2002/0197275 | A1 * | 12/2002 | Sunvold et al. .......... 424/195.18 |
| 2004/0038269 | A1 | 2/2004 | Birnboim |

FOREIGN PATENT DOCUMENTS

| | | |
|---|---|---|
| CA | 2236240 | 10/1999 |
| EP | 0273015 | 6/1988 |
| EP | 273015 A2 * | 6/1988 |
| EP | 0586024 | 3/1994 |
| EP | 0734684 | 10/1996 |
| EP | 1207208 | 5/2002 |
| JP | H6-78282 | 11/1994 |
| WO | WO 89/06704 | 7/1989 |
| WO | WO 91/02740 | 3/1991 |
| WO | WO 97/05248 | 2/1997 |
| WO | WO 97/48492 | 12/1997 |
| WO | WO 98/44158 | 10/1998 |
| WO | WO 99/29904 | 6/1999 |
| WO | WO 01/34844 | 5/2001 |
| WO | WO 01/60517 | 8/2001 |
| WO | WO 02/44691 | 6/2002 |
| WO | WO 03/104251 | 12/2003 |

OTHER PUBLICATIONS

English translation of specification for EP 273015 A2, http://worldwide.espacenet.com.*
English translation of claims for EP 273015 A2, http://worldwide.espacenet.com.*
Birnboim, "Effect of Lipophilic Chelators on Oxyradical-Induced DNA Strand Breaks in Human Granulocytes: Paradoxical Effect of 1,10-Phenanthroline," *Archives of Biochemistry and Biophysics* 294(1):17-21 (1992).
Birnboim, "Extraction of High Molecular Weight RNA and DNA from Cultured Mammalian Cells," *Methods in Enzymology* 216:154-160 (1993).
Birnboim and Doly, "A Rapid Alkaline Extraction Procedure for Screening Recombinant Plasmid DNA," *Nucleic Acids Research* 7(6):1513-1524 (1979).
Birnboim and Jevcak, "Fluorometric Method for Rapid Detection of DNA Strand Breaks in Human White Blood Cells Produced by Low Doses of Radiation," *Cancer Research* 41:1889-1892 (1981).
Clarke and Martell, "Stabilities of the Alkaline Earth and Divalent Transition Metal Complexes of the Tetraazamacrocyclic Tetraacetic Acid Ligands," *Inorganica Chimica Acta* 190:27-36 (1991).
French et al., "Ultra-Rapid DNA Analysis Using HyBeacon™ Probes and Direct PR Amplification from Saliva," *Molecular and Cellular Probes* 16:319-326 (2002).
Garcia-Closas et al., "Collection of Genomic DNA From Adults in Epidemiological Studies by Buccal Cytobrush and Mouthwash," *Cancer Epidemiology, Biomarkers & Prevention* 10:687-696 (2001).
Heath et al. "Use of Buccal Cells Collected in Mouthwash as a Source of DNA for Clinical Testing," *Archives of Pathology and Laboratory Medicine* 125:127-133 (2001).
Hiraide et al., "Speciation of Iron in River Water," *Analytical Sciences* 4:605-609 (1988).
Loens et al., "Detection of Mycoplasma Pneumoniae in Spiked Clinical Samples by Nucleic Acid Sequence-Based Amplification," *Journal of Clinical Microbiology* 40(4):1339-1345 (2002).
Lum and Marchand, "A Simple Mouthwash Method for Obtaining Genomic DNA in Molecular Epidemiological Studies," *Cancer Epidemiology, Biomarkers & Prevention* 7:719-724 (1998).
Nilsson et al., "Real-Time Monitoring of DNA Manipulations Using Biosensor Technology," *Analytical Biochemistry* 224:400-408 (1995).
Pershadsingh and McDonald, "A High Affinity Calcium-Stimulated Magnesium-Dependent Adenosine Triphosphatase in Rat Adipocyte Plasma Membranes," *Journal of Biological Chemistry* 255(9):4087-4093 (1980).
Roberts et al., "UV Laser Machined Polymer Substrates for the Development of Microdiagnostic Systems," *Analytical Chemistry* 69:2035-2042 (1997).
Rymaszewski et al., "Estimation of Cellular DNA Content in Cell Lysates Suitable for RNA Isolation," *Analytical Biochemistry* 188:91-96 (1990).
Seutin et al., "Preservation of Avian Blood and Tissue Samples for DNA Analyses," *Canadian Journal of Zoology* 69:82-90 (1991).
Terasaki et al., "Saliva as DNA Source for HLA Typing," *Human Immunology* 59:597-598 (1998).
van Schie and Wilson, "Saliva: A Convenient Source of DNA for Analysis of Bi-Allelic Polymorphisms of Fcγ Receptor IIA (CD32) and Fcγ Receptor IIIB (CD16)," *Journal Immunological Methods* 208:91-101 (1997).
Videira and Werner, "Assembly Kinetics and Identification of Precursor Proteins of Complex I from Neurospora Crassa," *European Journal of Biochemistry* 181:493-502 (1989).
International Preliminary Report on Patentability for PCT/CA2006/002009 dated Apr. 23, 2008.
Transmittal of the International Search Report and Written Opinion of the International Searching Authority for PCT/CA2006/002009 dated Mar. 30, 2007.
Transmittal of the International Search Report and the Written Opinion of the International Searching Authority for PCT/CA06/000380 dated Jul. 6, 2006.
Communication from European Patent Office regarding EP 03729743 dated Oct. 1, 2007.
Transmittal of the International Search Report for PCT/CA03/00869 dated Mar. 30, 2004.
Written Opinion for PCT/CA03/00869 dated Jul. 20, 2004.
Applicant's Letter in Response to the Written Opinion for PCT/CA03/00869 dated Jun. 3, 2004.
Rule 71(3) EPC Communication for European Patent Application No. 06846923.8 dated Mar. 8, 2011.
Office Action for Mexican Patent Application No. MX/a/2008/007253 dated Mar. 30, 2011 (English translation provided).
Australian Office Action (AU 2006324337) dated Aug. 18, 2011.
Notice of Reasons for Rejection for Japanese Patent Application No. 2008-543626, dated Jan. 17, 2012. (English Language Translation Provided).

* cited by examiner

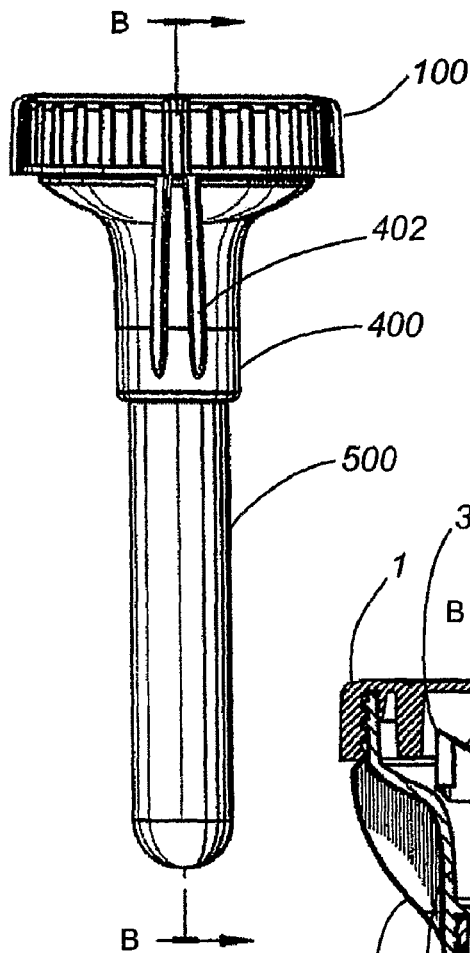
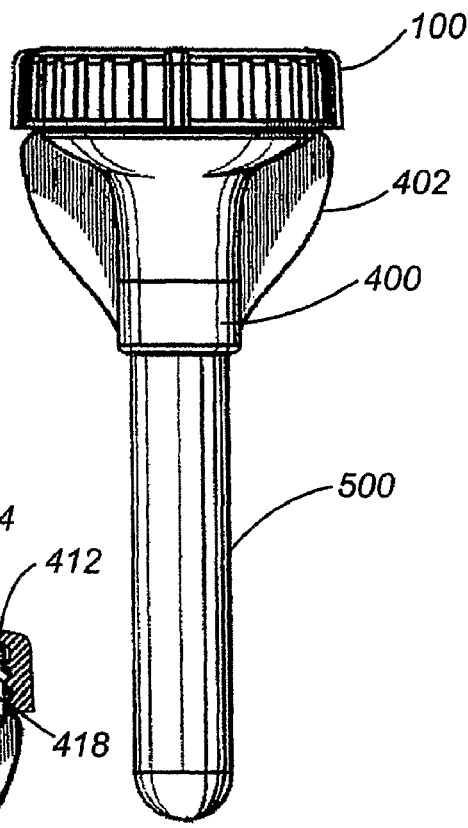
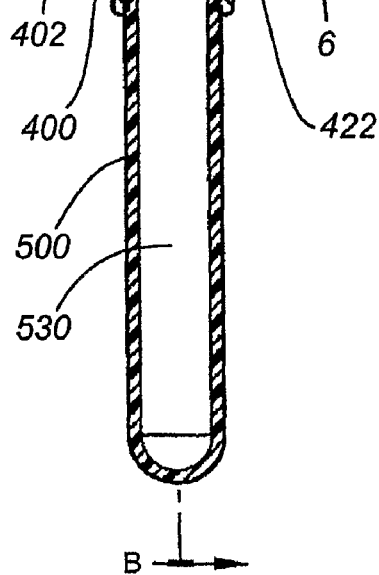
FIG. 15
FIG. 17
FIG. 16

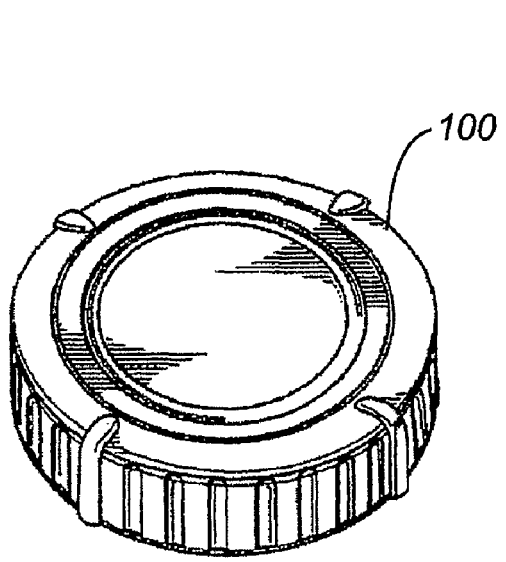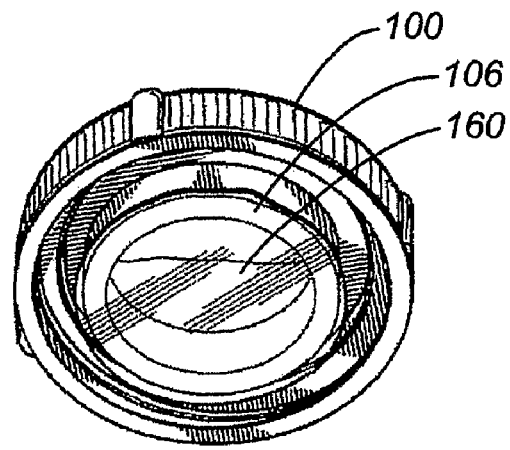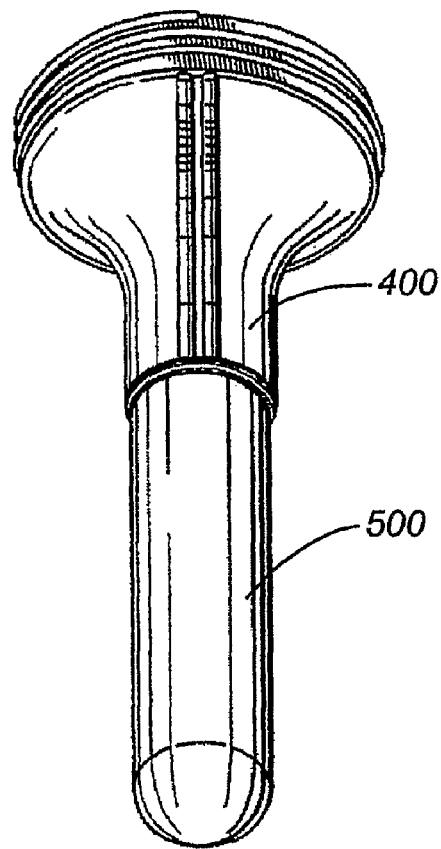
FIG. 18
FIG. 19

CONTAINER SYSTEM FOR RELEASABLY STORING A SUBSTANCE

RELATED APPLICATION

This application is the U.S. National Stage of International Application No. PCT/CA2006/002009, filed Dec. 11, 2006, which, in turn, claims the benefit of U.S. Application Ser. No. 60/748,977 filed on Dec. 9, 2005, the contents of which are hereby incorporated by reference in its entirety.

FIELD OF THE INVENTION

The field of the invention generally relates to a container system for releasably storing a substance.

BACKGROUND

It is often desirable to store a substance, such as a liquid, solid, gas, mixtures thereof, or the like, in a container prior to mixing the contents of the container with another material. For example, it may be desirable to package and store a compound, or compounds, in a container for shipping and/or safe storage and handling, prior to combining the compound (s) with another material. It may be desirable to package and store a toxic compound in a container, prior to combining such a toxic compound with a detoxifying material. As well, it is often desirable to keep a concentrated active ingredient separate from a diluent until immediately prior to use.

Moreover, it may be desirable to store and/or ship diagnostic and/or nucleic acid preserving compositions prior to combining such a substance with a biological sample.

Additionally, it may be desirable to keep a substance isolated from a donor until the donor's biological sample has been collected. This will help to prevent the donor from accidentally ingesting or spilling the substance.

It may also be desirable to inactivate pathogens/infectious particles in a biological sample by combining it with a stored substance prior to storage and/or shipping and/or handling of the sample.

It may also be desirable to store and/or ship diagnostic and/or nucleic acid preserving compositions after combining such a substance with a biological sample.

There are a variety of containers for holding substances separately in such a manner that a user may open a closure to combine the substances. Typically these containers are double compartment systems in which substances are stored separately and substances are combined by removal of the container closures by a user.

International PCT application WO 2003/104251 describes a container for collecting a biological sample from a subject, and subsequently mixing the collected sample with a composition intended to stabilize, preserve, or facilitate the recovery of components of the sample. This container has a first region for collecting a biological sample, a second region containing a composition for preserving a nucleic acid, and a barrier between the first region and the second region, which when in a closed position, maintains the sample and composition separate. The exemplified barrier of WO 2003/104251 is a pivoting partition. Attachment of a lid to the container forces the barrier to pivot from its original closed position spanning the container and thereby separating the first region and the second region, to an open position in which both regions are exposed to each other and contact between the composition contained in one region space and the biological sample contained in the other region is allowed. A drawback of this container is that it includes multiple parts (e.g., lid, vial, disk, rod, rod holder), which increases the cost of manufacture of the container. Additionally, because the disk is held in place by friction fit, there must be a high degree of precision for the manufacture of the components of the container.

There remains a need for an improved container system for releasably and reliably storing a substance.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention generally relates to a container system for releasably storing a substance.

In accordance with one aspect of the present invention, there is provided a container system for releasably storing a substance, comprising: a) a vial comprising a first open end for receiving a sample, a second end comprising a sample storage chamber and a piercing member; and b) a lid configured to removably engage said vial, said lid comprising a reservoir for holding the substance, and a pierceable membrane sealing the substance within said reservoir, wherein, when said system is closed by removable engagement of said vial with said lid, said vial and said lid are movable to a piercing position in which the piercing member disrupts the pierceable membrane to allow fluid communication between said reservoir and said chamber, wherein the chamber is sealed against leakage to the outside of the container system in the piercing position.

In accordance with another aspect of the present invention, there is provided a container system for releasably storing a substance, comprising: a) a vial comprising a chamber for retaining a sample b) a lid comprising a reservoir for holding the substance, and a pierceable membrane sealing the substance within said reservoir; and c) a funnel comprising a first open end for receiving said sample, a piercing member and a channel extending from said first open end to a second open end and being in fluid communication with said chamber, said funnel being removably attachable to said lid at said first open end and releasably or permanently attached to said vial at said second end, wherein, when said system is closed by removable attachment of said lid to said funnel, said system is movable to a piercing position in which the piercing member disrupts the pierceable membrane to allow fluid communication between said reservoir and said chamber, via said channel, wherein the chamber is sealed against leakage to the outside of the container system in the piercing position.

In accordance with another aspect of the present invention, there is provided a method of combining a substance with a biological sample, comprising: (a) providing a container system as described herein; (b) providing the sample to the chamber in the vial; and (c) closing said container system by removable attachment of the lid to the vial or funnel; and (d) piercing the membrane to release said substance into said chamber by moving the system to said piercing position.

In accordance with another aspect of the present invention there is provided a kit for releasably storing a substance comprising: a) a container system as described herein; and b) instructions for the use thereof.

BRIEF DESCRIPTION OF THE FIGURES

FIG. 15 is a side view of the container system depicted in FIG. 12;

FIG. 16 is a cross-sectional view of the container system of FIG. 12 taken along line B-B in FIG. 15;

FIG. 17 is a side perspective view of the container system depicted in FIG. 12;

FIG. 18 is a top perspective view of the container system depicted in FIG. 12, showing the lid and funnel separated;

FIG. 19 is a bottom side perspective view of the container system depicted in FIG. 12, showing the lid and funnel separated;

Figure 1:
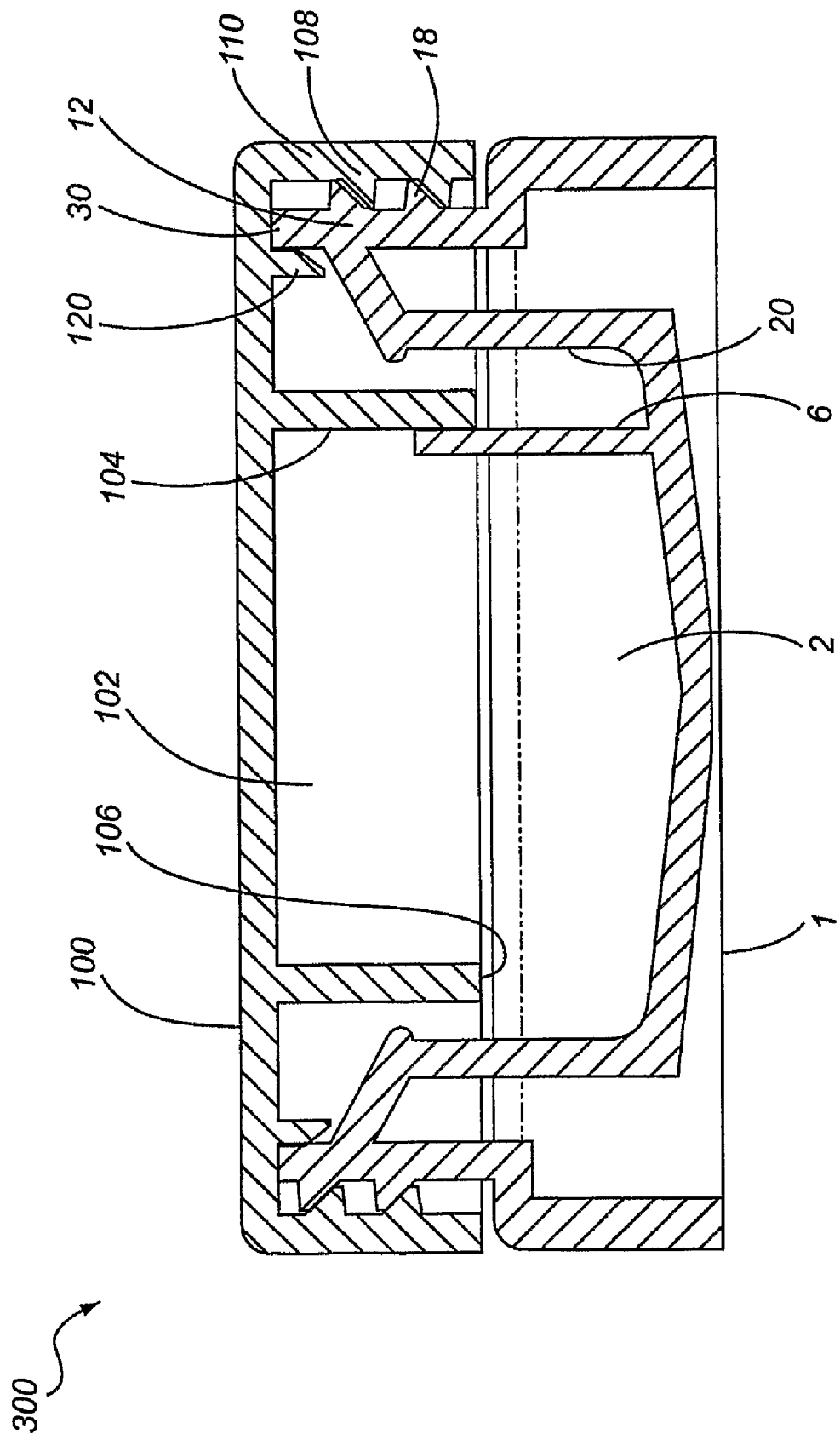
FIG. 1 is a cross-sectional view of a container system in accordance with one embodiment of the present invention, showing the lid and vial attached.
Figure 2:
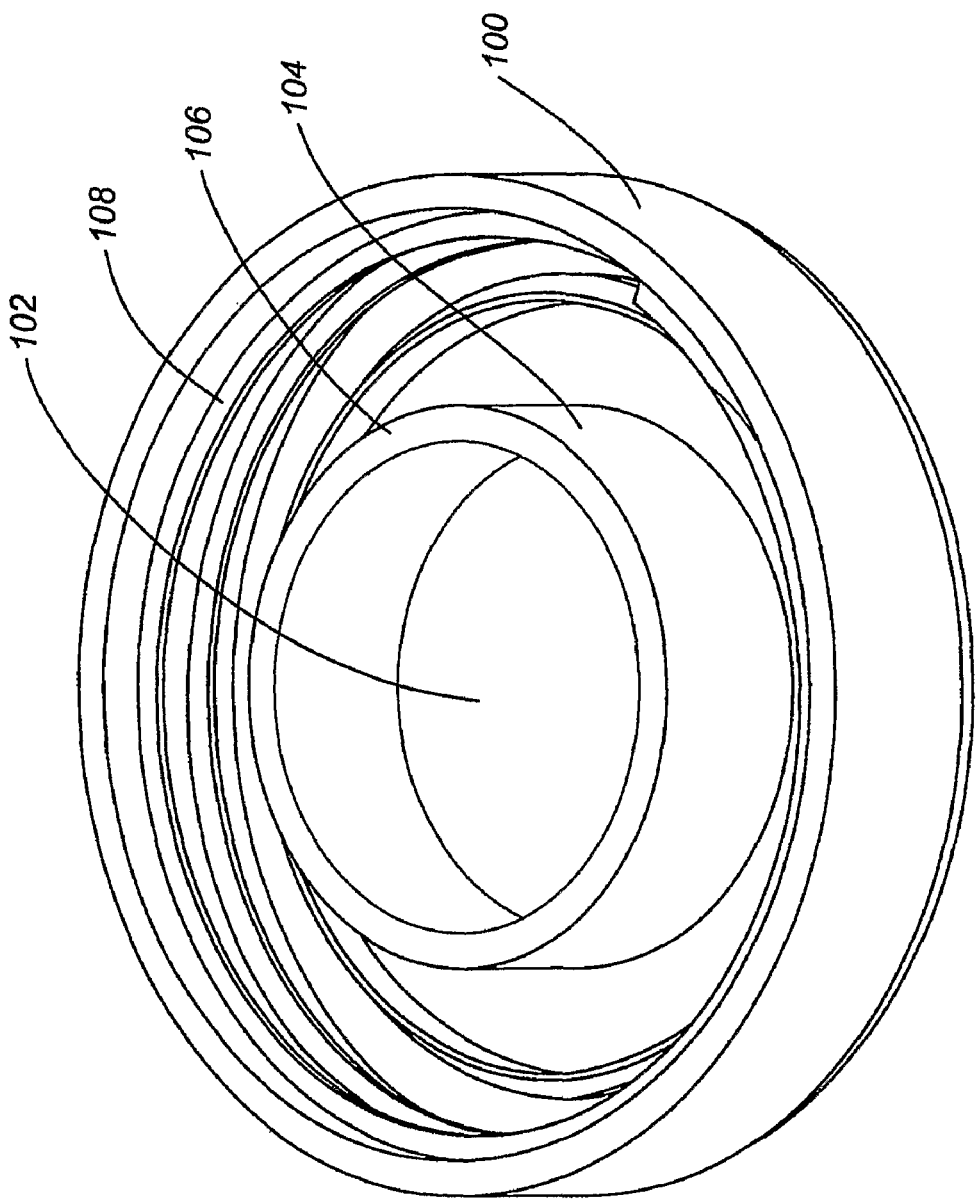
FIG. 2 is a perspective view of the interior of the lid of the container system depicted in FIG. 1.
Figure 3:
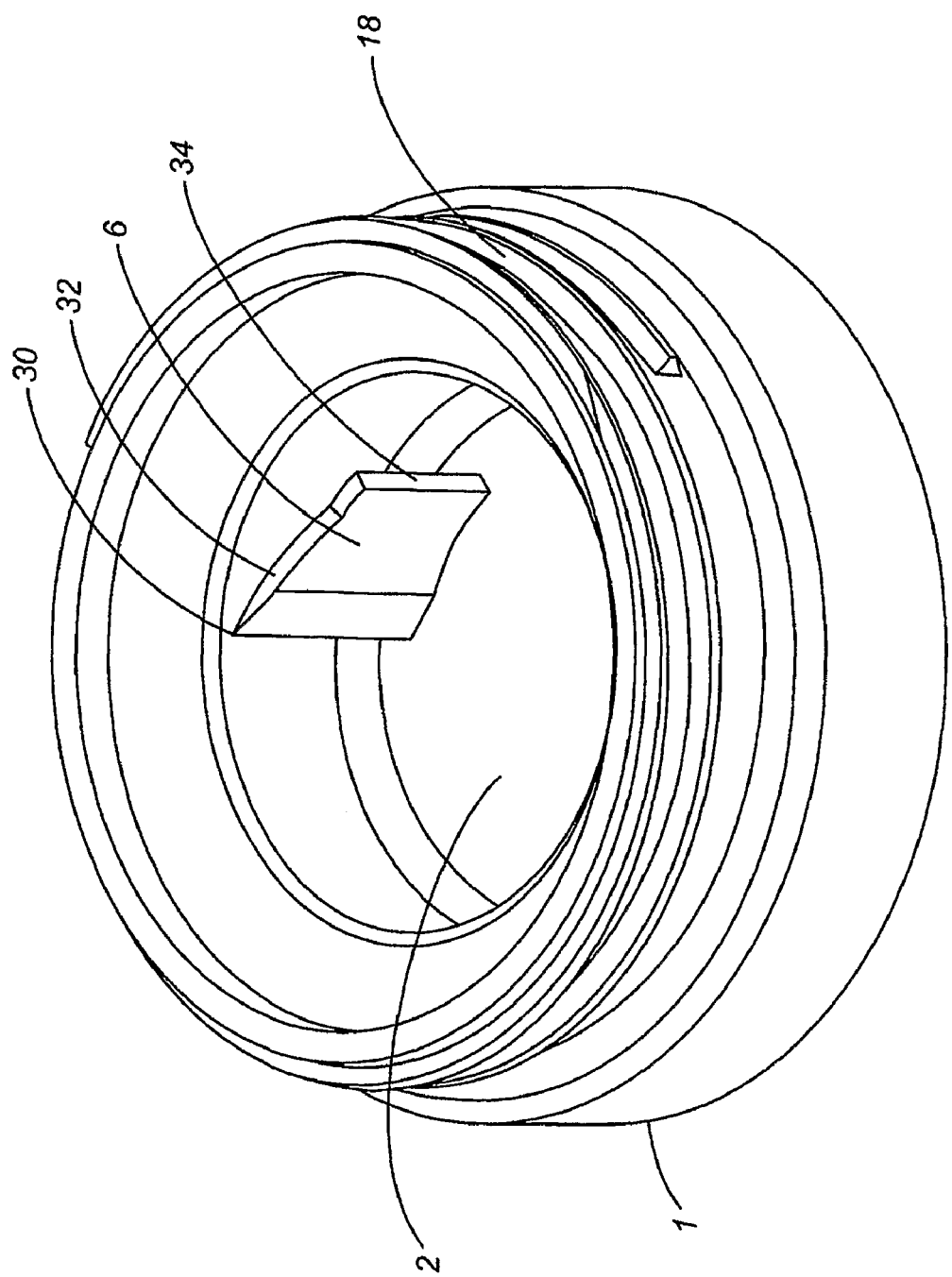
FIG. 3 is a perspective view of the interior of the vial of the container system depicted in FIG. 1.
Figure 4:
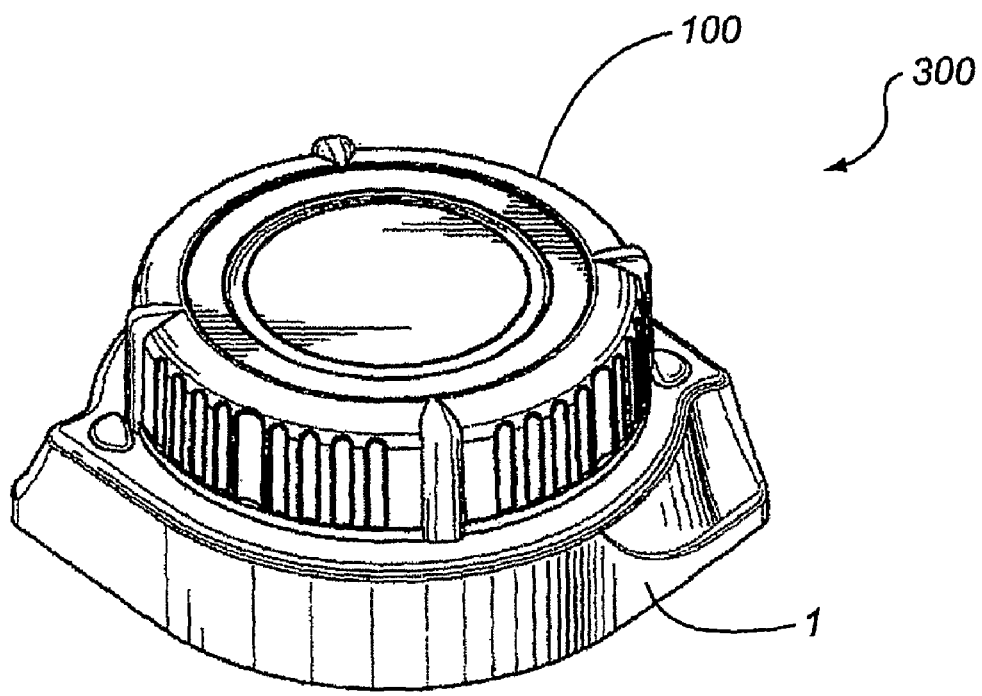
FIG. 4 is a perspective view of a container system in accordance with one embodiment of the present invention.
Figure 5:
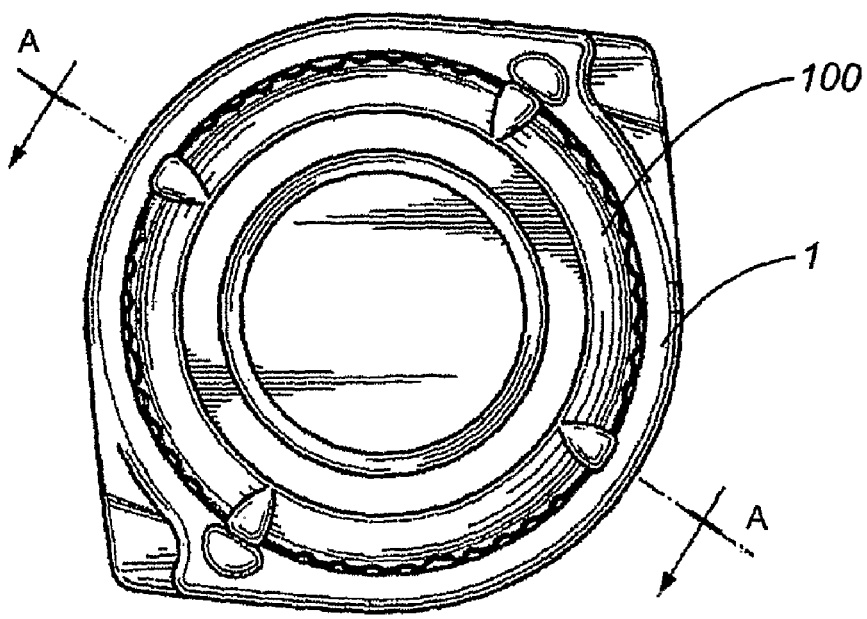
FIG. 5 is a top view of the container system depicted in FIG. 4.
Figure 6:
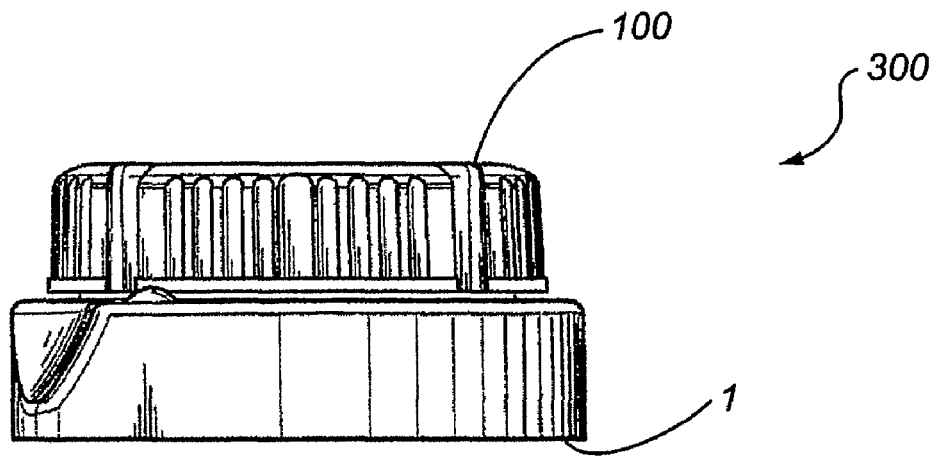
FIG. 6 is a side view of the container system depicted in FIG. 4.
Figure 7:
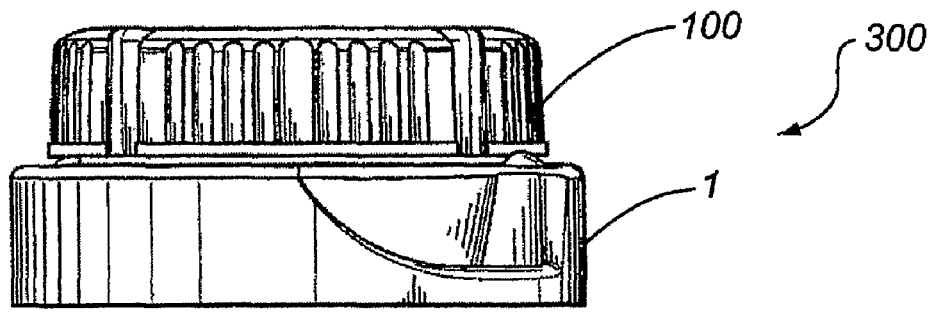
FIG. 7 is a side view of the container system depicted in FIG. 4.
Figure 8:
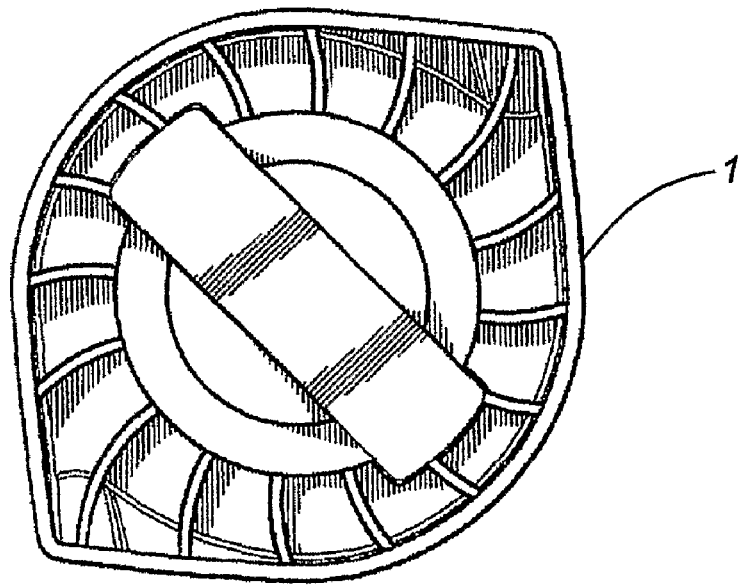
FIG. 8 is a bottom view of the container system depicted in FIG. 4.

The numbers in bold face type serve to identify the component parts that are described and referred to in relation to the drawings depicting various embodiments of the present invention. It should be noted that in describing various embodiments of the present invention, the same reference numerals have been used to identify the same or similar elements. Moreover, for the sake of simplicity, parts have been omitted from some figures of the drawings.

DETAILED DESCRIPTION OF THE INVENTION

As will be discussed in more detail below, the present invention provides a container system for releasably storing a substance.

The container system of the present invention has fewer parts and, thus, is less expensive and/or easier to manufacture, than previous containers. Additionally, the manufacturing tolerances can be less precise for the container system of the present invention, as compared to previous containers having separable compartments. Again, this reduces manufacturing cost, and makes accidental disruption of a sealed substance less likely. Additionally, in one example of the present invention, the container system includes a removable vial which is suitable for subsequent processing of samples and/or for use in robotic systems.

The container system of the present invention comprises a vial and a lid. Optionally, the container system additionally comprises a funnel that is permanently or removably attached to the vial and that sealingly engages the lid. The lid is configured to store a substance, and subsequently release the substance from the lid when the lid is sealingly attached to the vial, or the funnel. In use, the substance stored within the lid is released into the vial when the lid is attached to the vial or the funnel, if present.

In accordance with a specific embodiment of the present invention, the lid is suitable to store a substance to stabilize, preserve or facilitate the recovery of nucleic acid from a biological sample. In accordance with a related embodiment, the vial, or the combination of the funnel and vial is suitable for the collection of a biological sample from a subject.

Referring to the FIGS. 1-11 and 22-24, container system 300 comprises lid 100 and vial 1.

Lid

Lid 100 releasably stores a substance. Lid 100 is generally cylindrically shaped with at least one open end. Lid 100 can be a variety of shapes, as determined by the needs or preferences of the user and/or the intended application of use. The interior of lid 100 includes wall 104 that is positioned within lid 100 and defines reservoir 102 for holding a substance such as a liquid, solid, semi-solid, gas, mixtures thereof and the like. Wall 104 defines all or a portion of the perimeter of reservoir 102. Wall 104 includes sealing surface 106 which is for sealingly attaching pierceable membrane 160

Pierceable membrane 160 (depicted in FIG. 19) acts as a physical barrier to releasably store a substance within reservoir 102, when attached to sealing surface 106. Pierceable membrane 160 is made from material that is inert to the substance to be stored within the reservoir. Pierceable membrane 160 permits little or no diffusion of the substance through pierceable membrane 160 over time. Pierceable membrane 160 is made from a material that is suitable for the intended processing, storage and/or transportation conditions. In a specific embodiment, pierceable membrane 160 is heat and cold resistant such that it remains intact and pierceable at temperatures ranging from about −80° C. to about +70° C. In a specific embodiment, pierceable membrane 160 can be attached tightly enough to sealing surface 106 such that pierceable membrane 160 will not be disrupted by vacuum pressures. Pierceable membrane 160 can be made from a variety of materials including polypropylene. Desirably, pierceable membrane 160 is made from the same material as wall 104. The thickness of pierceable membrane 160 can vary according to application of use, and preference of the user. Desirably, pierceable membrane 160 has a thickness of about two thousandths of an inch. However, the specific thickness of the membrane will be determined by factors such as, nature of the substance, nature of the sample, overall dimensions of the container system and chemical composition of the membrane.

A variety of methods of attaching pierceable membrane 160 to sealing surface 106 can be used, and is dependent on the material used to make lid 100, the substance stored within reservoir 102, and/or the characteristics of membrane 160. Such methods of attachment include use of adhesive(s), heat-sealing treatment, fasteners, or any combination thereof, and the like. Desirably, heat-sealing is used to attach pierceable membrane 160 to sealing surface 106. As will be clear to the skilled worker, the type of pierceable membrane, the physical and/or chemical properties of the pierceable membrane will be dependent upon, in part, the composition to be stored. Desirably pierceable membrane 160 is inert with respect to the intended use, stored substance and sample of the container system.

In the specific embodiments depicted in the Figures, lid 100 comprises internal helical threads 108 on the inner surface of outer wall 110, which are adapted to engage external helical threads 18 on the outer surface of wall 12 on vial 1. As would be appreciated by a skilled worker, alternative means for releasable attachment of lid 100 to vial 1 can be used in the container system of the present invention, provided that lid 100 and vial 1 are movable to a piercing position, as discussed in greater detail below.

Lid 100 and reservoir 102 can be sized to accommodate a range of volumes of a substance. In the specific embodiment in which the substance is a nucleic acid preservative for use with a saliva sample, reservoir 102 accommodates about 1 ml to about 4 ml of a substance. The choice of material used to manufacture lid 100 is dependent upon a number of factors including manufacturing constraints, chemical suitability, and the like. In the specific embodiment in which the substance is a nucleic acid preservative for use with a saliva sample, lid 100 is made from plastics such us polypropylene, medium-density polyethylene (MDPE), high-density polyethylene (HDPE), polyethylene and the like. Desirably, lid 100 is polypropylene. The materials of lid 100 may be opaque, transparent or translucent, depending on the desired application. For example, an opaque material can be used to store a light sensitive composition(s). A transparent or translucent material is desirable if a visual (e.g., colour) indicator is present in the stored substance. Lid 100 and reservoir 102 can be manufactured to include gradations to demarcate the quantity of the substance stored within reservoir 102. The outer surface of lid 100 can also include a labelling area for a user to identify the contents of the lid. The outer surface of lid 100 may also include a region to affix or emboss a logo and/or other markings.

In accordance with one embodiment of the present invention, wall 104 has a generally cylindrical shape sized to fit within the interior of lid 100. It will be clear that the shape and size of well 104 is dependent upon the intended use of the container system. Lid 100 may be constructed from a single piece of material that includes wall 104, or wall 104 may be removably attached to lid 100. Desirably, lid 100 is formed from a single piece of material.

Vial

In accordance with one embodiment of the present invention, vial 1 is generally cylindrically shaped with at least one open end. Vial 1 can be a variety of shapes, as determined by the needs or preferences of the user and/or application of use. The interior of vial 1 comprises chamber 2 for receiving a sample such as a liquid, solid, semi-solid, mixtures thereof and the like. Desirably, chamber 2 is configured to receive a biological sample, for example a sputum sample, such as saliva.

Vial 1 comprises a first open end for receiving said sample, and a second end comprising chamber 2. In one example, said second end is a second closed end. In another example, said second end is a second open end.

In one example, the width of the first open end of vial 1 is approximately equivalent to the width of the second end.

In another example, the first open end of vial 1 is generally wider than the second end vial 1. In this example, the generally wider first open end facilitates sample collection by, for example, acting similar to a funnel.

Figure 22:
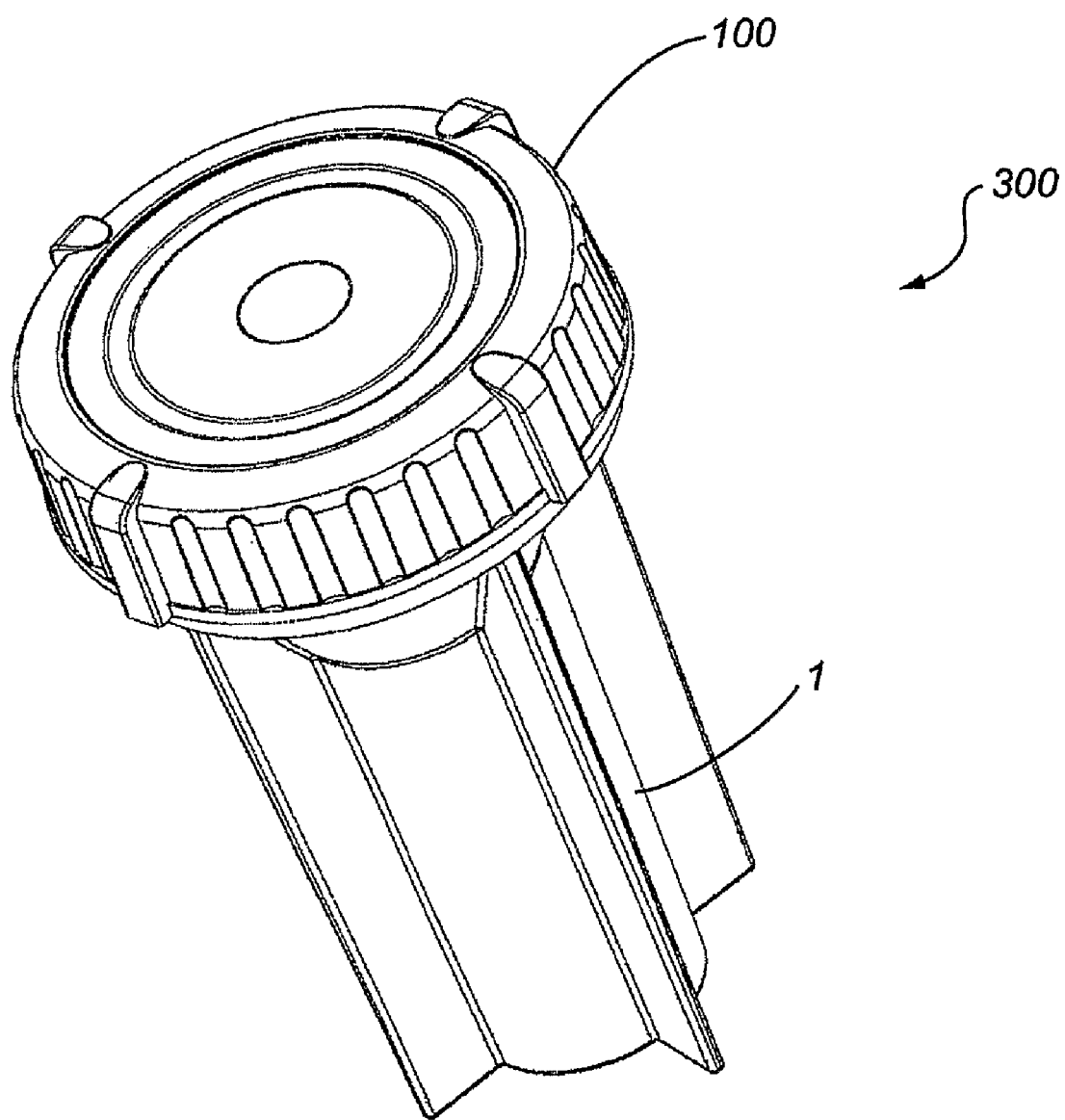
FIG. 22 is a side perspective view a container system in accordance with one embodiment of the present invention.
Figure 23:
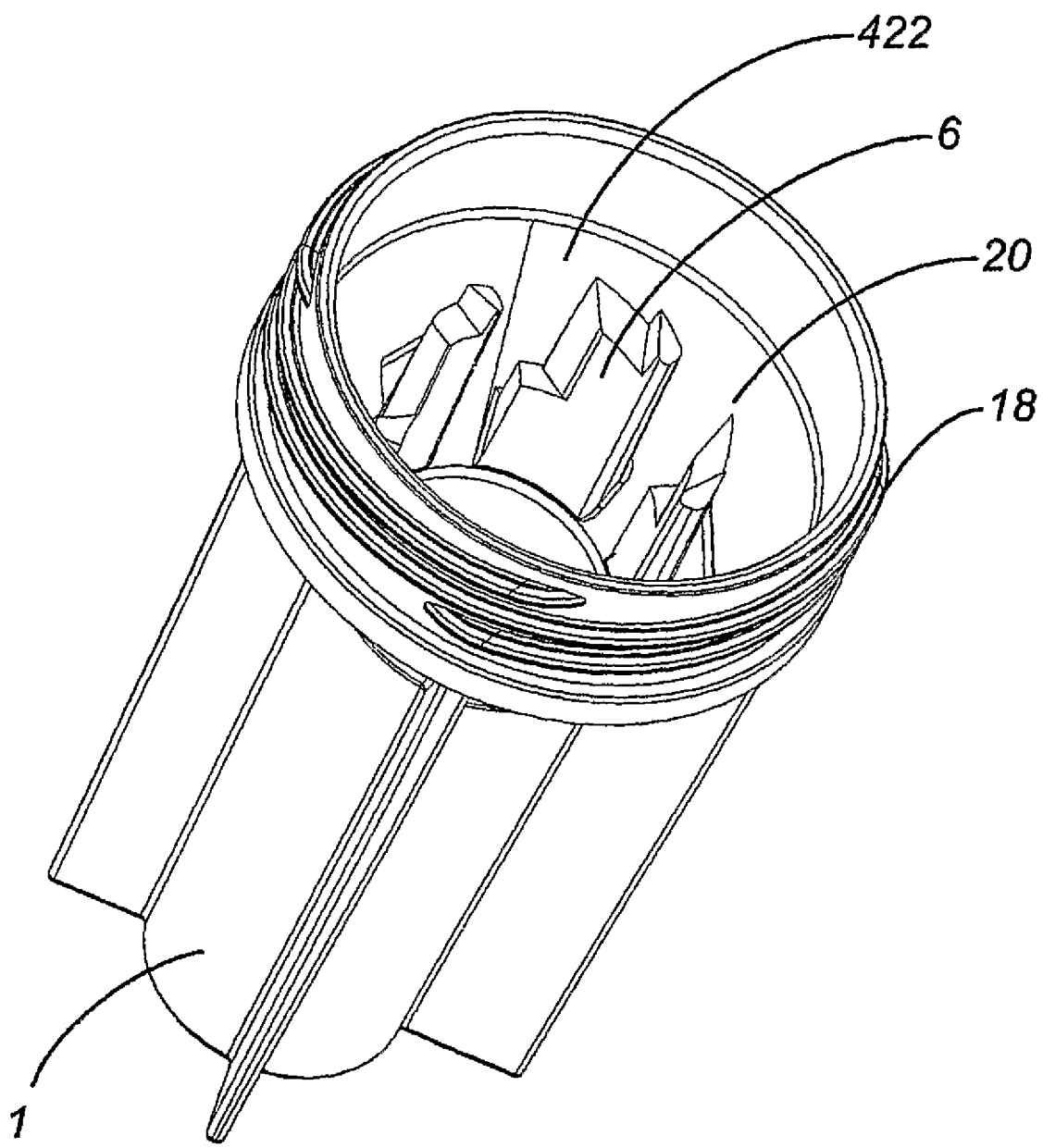
FIG. 23 is a top perspective view of the vial portion of the container system depicted in FIG. 22, showing the vial.
Figure 24:
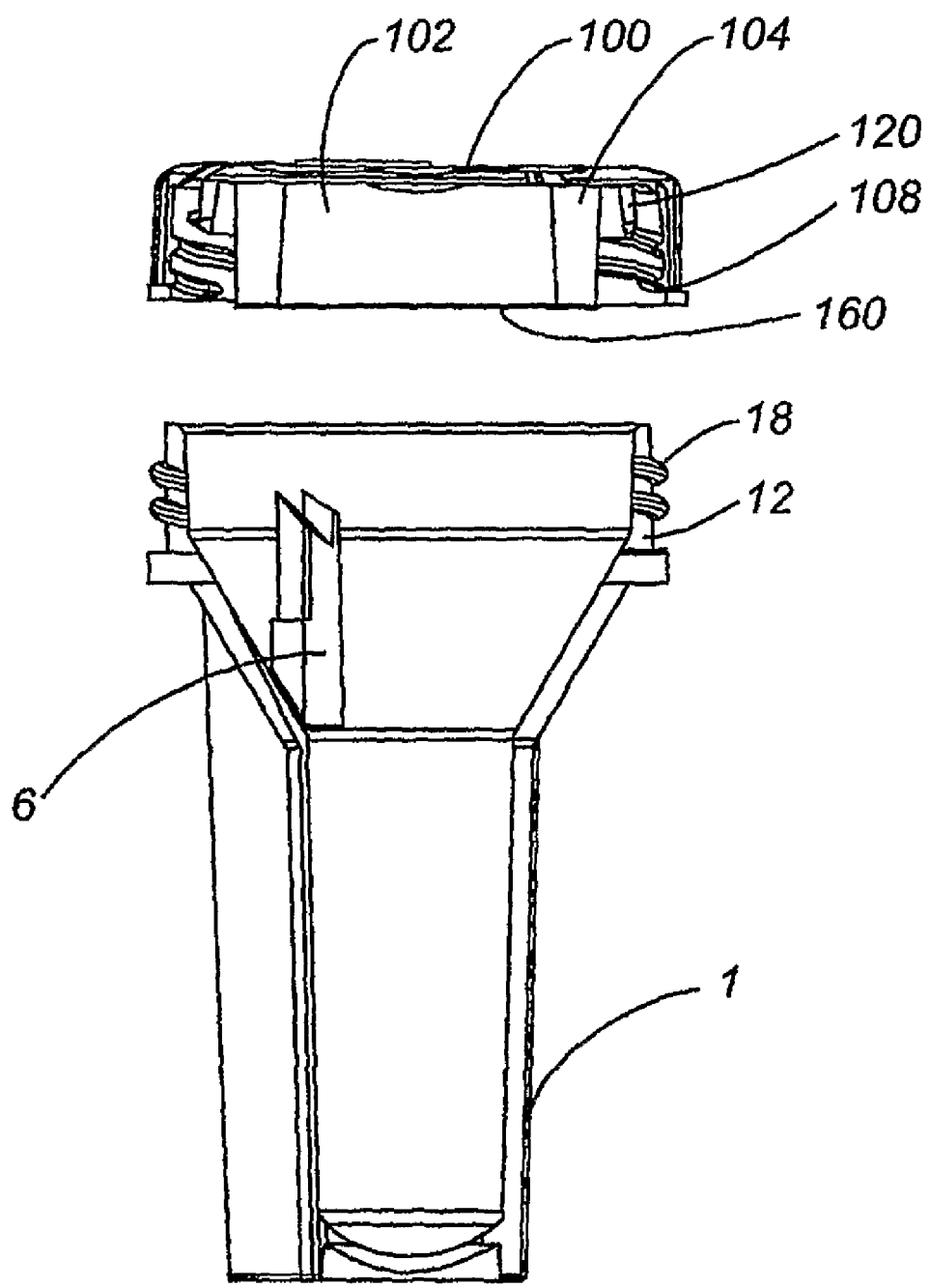
FIG. 24 is a cross-sectional view of the lid of the container system depicted in FIG. 22.

In accordance with one embodiment, and as shown in FIG. 22-24, container system 300 comprises a funnel fixedly attached to, or integral with, vial 1. In the case in which the funnel is fixedly attached to, or integral with vial 1, it can also be characterised as a vial having a wide mouth opening for receiving a sample. The wide mouth or funnel characteristics can make it easier for a subject to provide a sample.

Vial 1 and chamber 2 can be sized to accommodate a range of volumes of a sample. In the specific embodiment in which the substance is a nucleic acid preservative for use with a saliva sample, chamber 2 accommodates about 1 ml to about 4 ml of a sample. In another specific embodiment, chamber 2 accommodates about 1 ml to about 16 ml of a sample.

Vial 1 comprises at least one piercing member 6. In the specific embodiment depicted in FIGS. 1-11 piercing member 6 extends from a base surface of chamber 2. In one example, piercing member 6 extends approximately perpendicular from the base. In another example, piercing member 6 is angled inwardly or outwardly toward the open end of vial 1. Alternatively, piercing member 6 extends from an interior surface of said vial. In one example, piercing member 6 extends from an interior surface of said vial and is angled inwardly or outwardly toward the open end of vial 1.

Figure 9:
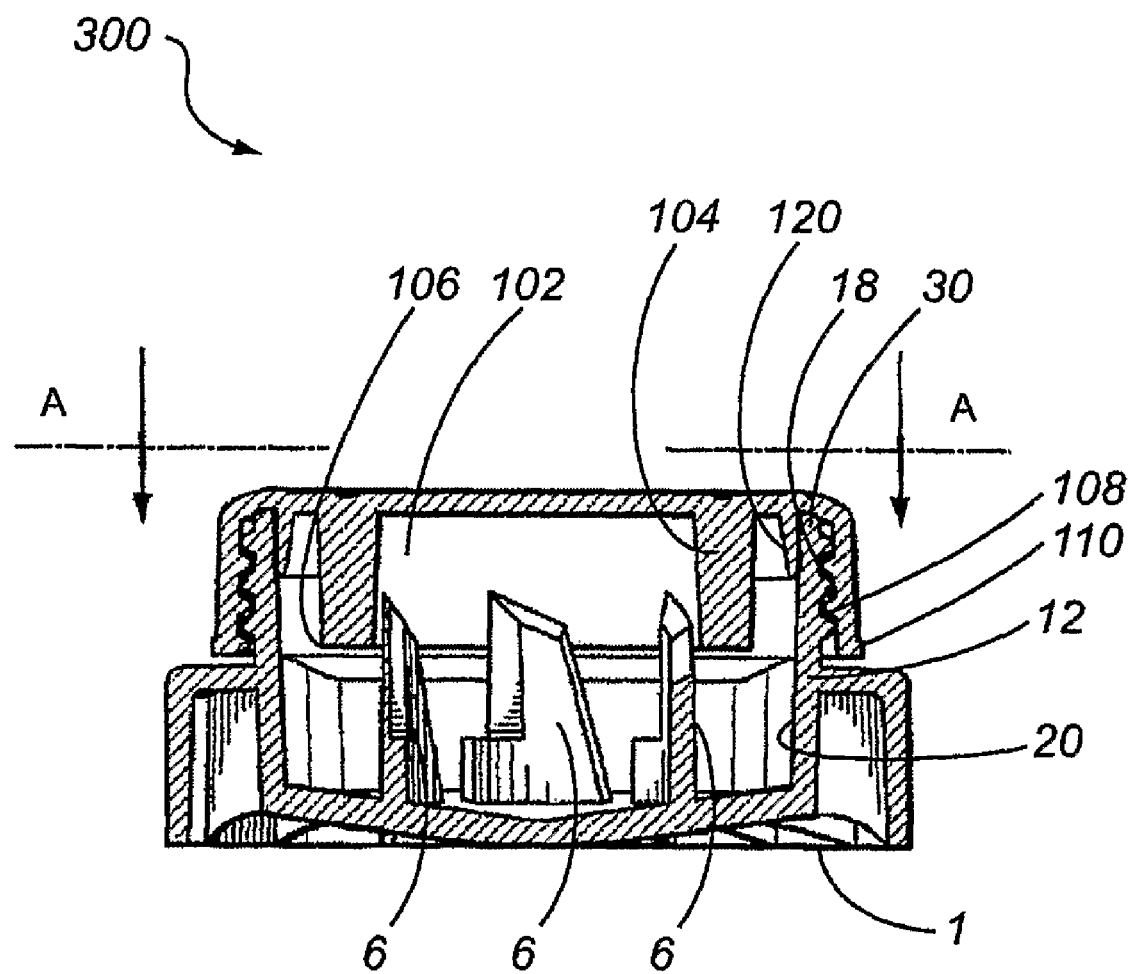
FIG. 9 is a cross-sectional view of the container system of FIG. 4 taken along line A-A in FIG. 5.
Figures 10, 11:
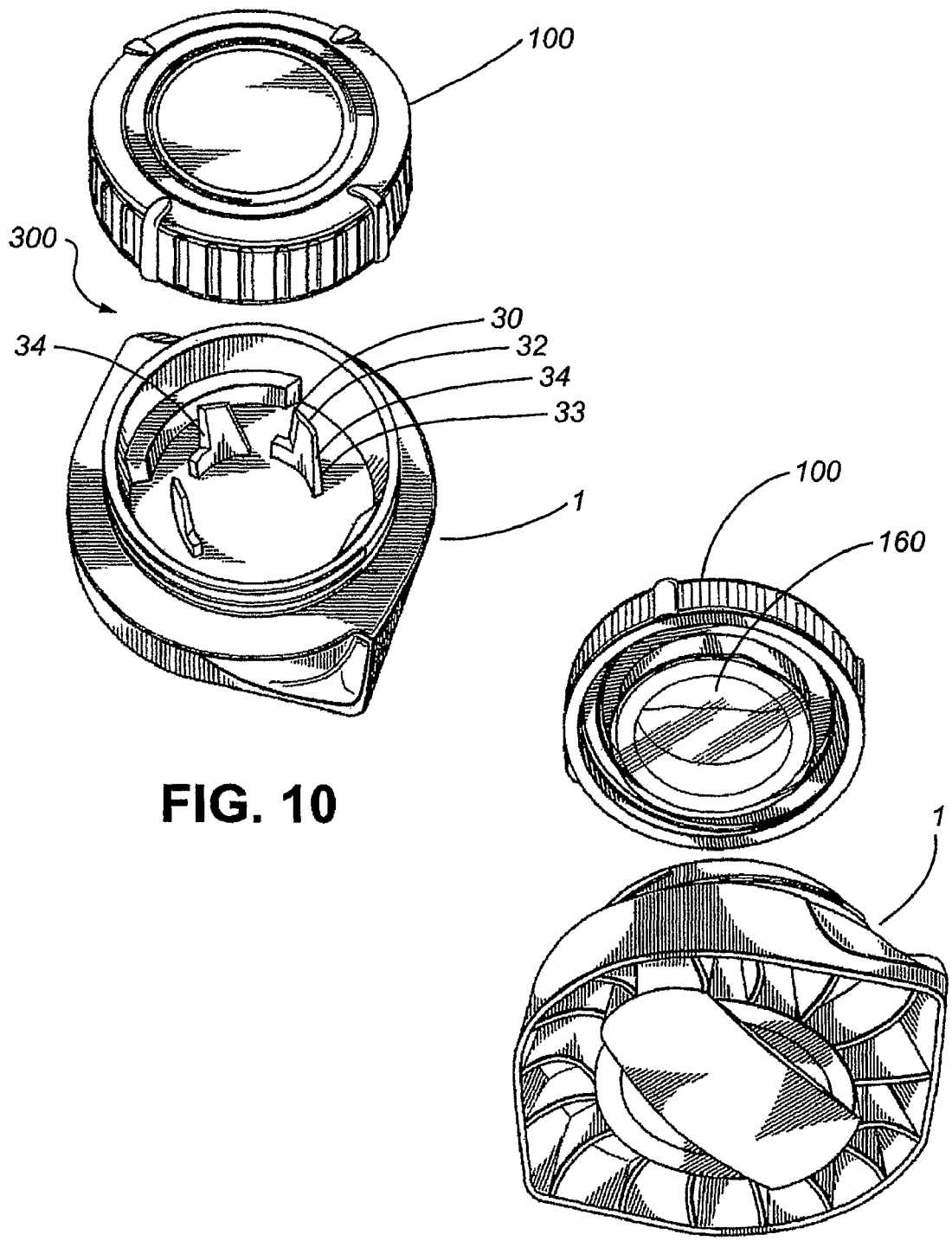
FIG. 10 is a top perspective view of the container system depicted in FIG. 4 showing the lid and vial separated.
FIG. 11 is a bottom perspective view of the container system depicted in FIG. 4 showing the lid and vial separated.
Figure 12:
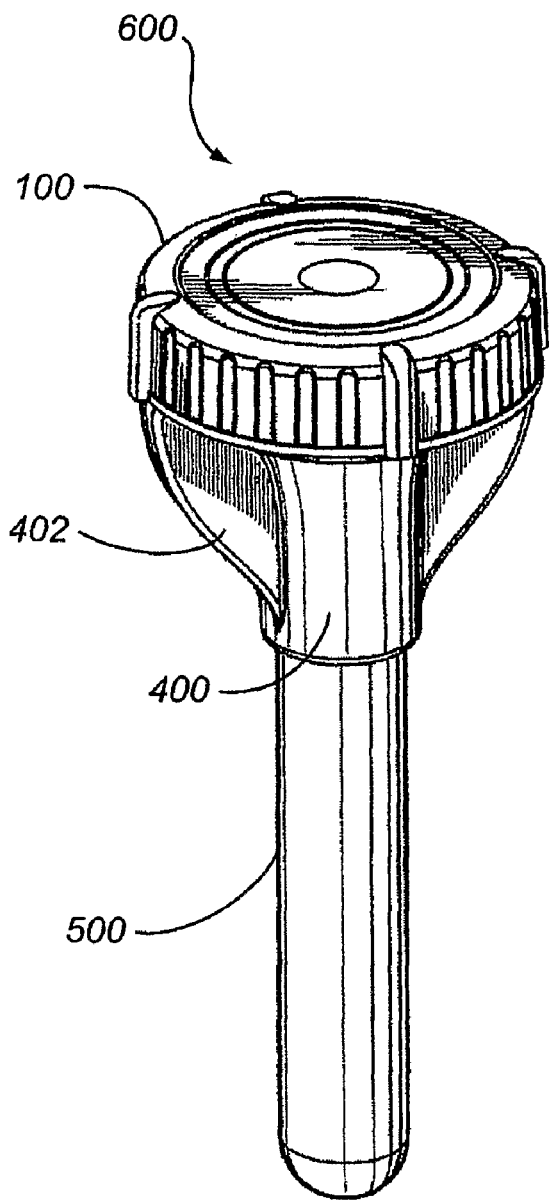
FIG. 12 is a side perspective view a container system in accordance with one embodiment of the present invention.
Figure 13:
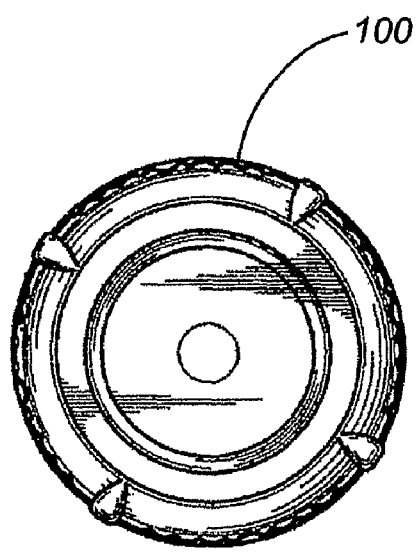
FIG. 13 is a top view of the container system depicted in FIG. 12.
Figure 14:
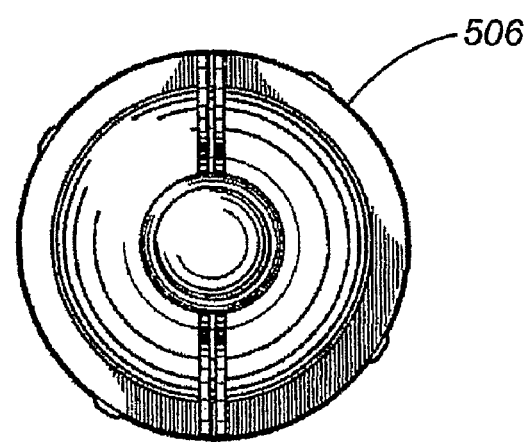
FIG. 14 is a bottom view of the container system depicted in FIG. 12.
Figure 20:
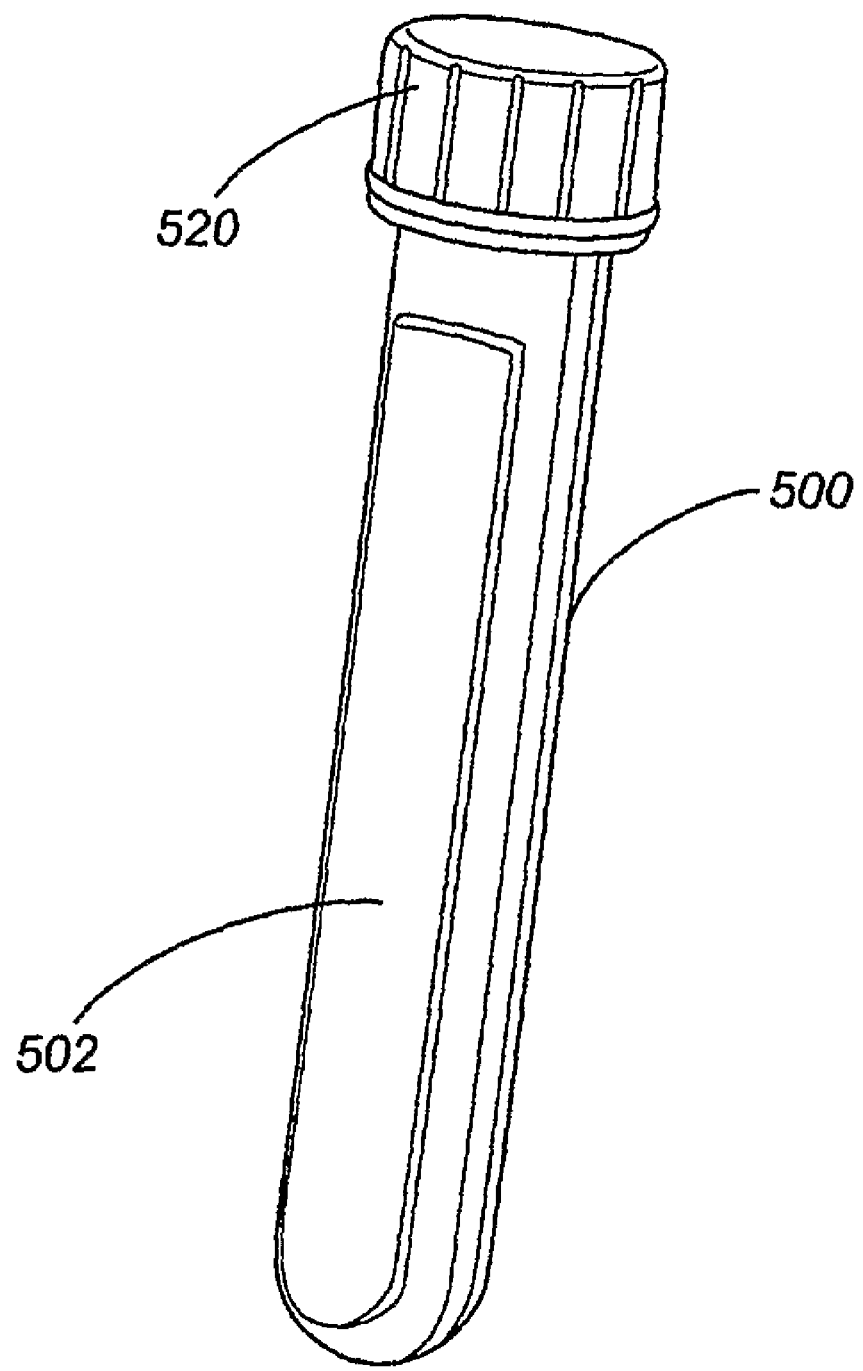
FIG. 20 is a side view of the vial and cap of the container system depicted in FIG. 9.

In one example, there is one piercing member 6 within chamber 2. In an alternative example, there is a plurality of piercing members 6, for example, two piercing members, three piercing members or more than three piercing members. In one example the piercing members are arranged in a generally semicircular fashion. In a specific example, in the case of three piercing members, the piercing members are arranged in a generally semicircular fashion, as depicted in FIGS. 9, 10 and 23.

Piercing member 6 can be approximately trapezoidal in shape and includes first cutting edge 33 having pointed end 30 at one corner of the trapezoid and a second end at a second corner of the trapezoid where cutting edge 32 intersects side wall 34. Optionally, side wall 34 also includes cutting edge 33, which extends from cutting edge 32.

Container system 300 further includes a means for sealing attachment of lid 1 to vial 100. Such sealing means act to ensure that the contents of vial 1 remain sealed with chamber 2 when lid 100 is attached to vial 1.

In one example, lid 100 and vial 1 are movable between an open position and a piercing position. In a specific example, lid 100 is initially attached to vial 1 by threadingly engaging internal and external threads 108 and 18 with a twisting motion. Initially, lid 100 and vial 1 are threadingly connected, but piercing member 6 does not disrupt pierceable membrane 160 and end portion 30 of wall 12 engages sealing wall 120. For example, as depicted in FIG. 9, sealing wall 120 extends downwardly and outwardly from the interior of lid 100. This type of sealing mechanism is similar to a wipe seal that would be well known to the skilled worker. Thus, initially, chamber 2 is maintained out of fluid communication with reservoir 102 by pierceable membrane 160.

In an alternate example, lid 100 and vial 1 are movable between a first position and a piercing position. In a specific example, lid 100 is initially attached to vial 1 by threadingly engaging internal and external threads 108 and 18 with a twisting motion and thereby moved to the first position. In moving lid 100 and vial 1 to the first position, lid 100 and vial 1 are threadingly connected, but piercing member 6 does not disrupt pierceable membrane 160. In the first position, end portion 30 of wall 12 sealingly engages sealing wall 120. For example, as depicted in FIG. 9, sealing wall 120 extends downwardly and outwardly from the interior of lid 100. This type of sealing mechanism is similar to a wipe seal that would be well known to the skilled worker. Thus, in the first position, chamber 2 is sealed against leakage to the outside of the container system by sealing engagement of wall 12 with sealing wall 120 and maintained out of fluid communication with reservoir 102 by pierceable membrane 160.

A worker skilled in the art will recognize that there are known alternative sealing structures that can be incorporated into the present system for ensuring that chamber 2 is sealed against leakage to the outside of the container system. Such alternatives are considered to be within the scope of the present invention.

Continued twisting moves lid 100 and vial 1 from the open position, or the first position, to the piercing position, in which movement of lid 100 and vial 1 together results in disruption of pierceable membrane 160 by piercing member 6, and the release of the substance within reservoir 102 into chamber 2.

In operation, in moving to the piercing position, pointed end 31 of piercing member 6 is brought into contact with pierceable membrane 160 and pierces pierceable membrane 160. Continued twisting moves cutting edge 32 through pierceable membrane 160, disrupting pierceable membrane 160, and thereby producing an opening in the sealing membrane to enable the substance to enter chamber 2. It will be clear that if more than one piercing member is present, less twisting of lid 100 and vial 1 is required to generate an opening. When three piercing members are present, a suitable opening is obtainable in about one quarter of a turn. Desirably, pierceable membrane 160 is not completely removed from sealing surface 106. Thus, in the piercing position, piercing member 6 disrupts pierceable membrane 160 to allow fluid communication between reservoir 102 and chamber 2.

The distance between piercing member 6 and wall 104 will vary according to the needs and preferences of the user. The distance between piercing member 6 and wall 104 can vary from being generally flush with one another, to being generally separated from one another.

It will be clear to the skilled worker that length, rigidity and the like, of piercing member 6 is selected such that it is sufficient to disrupt pierceable membrane 160 when lid 100 and vial 1 are in the piercing position, and not disrupt the pierceable membrane 160 when lid 100 and vial 1 are in the open or first position.

The choice of the material of vial 1 will be dependent upon a number of factors including manufacturing constraints, chemical suitability, and the like. Additionally, the construction material of lid 1 may be same or different as that used to make reservoir 6. In the specific embodiment in which the substance is a nucleic acid preservative for use with a saliva sample, vial 1 is made from plastics such us polypropylene, medium-density polyethylene (MDPE), high-density polyethylene (HDPE), polyethylene and the like. Desirably, vial 1 is HDPE.

In accordance with another aspect of the present invention, the container system comprises a lid, a funnel and a vial.

Referring to the FIGS. 12-21, container system 600 comprises lid 100 and funnel 400 and vial 500.

Lid

Lid 100 releasably stores a substance, as described above.

Funnel

Funnel 400 includes a first open end for receiving a sample, a second open end for removable or fixed attachment to vial 500. In one embodiment, funnel 400 is integral with vial 500. The interior of funnel 400 comprises interior channel 422 extending therethrough for maintaining the first open end and the second open end in fluid communication and for receiving a sample such as a liquid, solid, semi-solid, mixtures thereof and the like. Funnel 400 can be a variety of shapes, as determined by the needs or preferences of the user and/or application of use. Desirably, interior channel 422 is configured to receive a biological sample. For example, the biological sample is a sputum sample, such as saliva. Interior channel 422 can be sized accommodate a range of volumes of sample.

In the specific embodiments depicted in the Figures, lid 100 comprises internal helical threads 108 on the inner surface of outer wall 110, which are adapted to engage external helical threads 418 on the outer surface of wall 412 on funnel 400. As would be appreciated by a skilled worker, alternative means for releasable attachment of lid 100 to funnel 400 can be used in the container system of the present invention, provided that lid 100 and funnel 400 are movable to the piercing position, as discussed in greater detail above.

Funnel 400 comprises at least one piercing member 6. In accordance with the embodiment depicted in FIGS. 12-21, piercing member 6 extends from an interior surface (interior side wall 420) of funnel 400. In one example, piercing member 6 is angled inwardly or outwardly toward pierceable membrane 160. Other arrangements of piercing member 6 can be used, as would be readily appreciated by the skilled worker.

In one example, there is one piercing member 6 within interior channel 422. In an alternative example there is a plurality of piercing members, for example, two piercing members, three piercing members or more than three piercing members. In the case of three piercing members, desirably the piercing members are arranged in a generally semicircular fashion, as shown in FIG. 18.

As above, piercing member 6 can be approximately trapezoidal in shape and includes first cutting edge 33 having pointed end 30 at one corner of the trapezoid and a second end at a second corner of the trapezoid where cutting edge 32 intersects side wall 34. Optionally, side wall 34 also includes cutting edge 33, which extends from cutting edge 32.

Container system 600 further includes a means for sealing attachment of lid 1 to funnel 400. Such sealing means act to ensure that the contents of vial 1 remain sealed with chamber 2 when funnel 400 and vial 500 are attached to vial 1.

Optionally, funnel 400 includes outwardly extending ribs 402 that can used by a user to twist funnel 400 and lid 100, and/or funnel 400 and vial 500.

The choice of the material of funnel 400 will be dependent upon a number of factors including manufacturing constraints, chemical suitability, and the like. Additionally, the construction material of funnel 400 may be same or different as that used to make lid 100 and collection vial 500. In the specific embodiment in which the substance is a nucleic acid preservative for use with a saliva sample, funnel 400 is made from plastics such us polypropylene, high-density polyethylene (HDPE), polyethylene, medium-density polyethylene (MDPE), or any combination thereof, and the like. Desirably, vial 1 is HDPE.

In a specific example, lid 100 is polypropylene, vial 500 is polypropylene and funnel 400 is HDPE.

Vial

Vial 500 (or collection vial 500) is generally cylindrically shaped with an open end for removable or fixed attachment to the second end of funnel 400, and chamber 530 for receiving a sample. Vial 500 can be a variety of shapes, as determined by the needs or preferences of the user and/or application of use, and can be specifically manufactured for use in the container system of the present invention or can be a commercially available vial. As noted above, and in one embodiment, funnel 400 is integral with vial 500. When the container system is used for laboratory purposes, desirably, vial 500 is sized to fit within a standard test tube rack such as that typically used in biological sample processing. In one example, vial 500 conforms with industry-standard dimensions for blood collection tubes (e.g., 13 mm×75 mm). Desirably vial 500 is suitable for use with robotic DNA purification systems (e.g., the Beckman BioMek™ FX). Desirably, vial 500 is commercially availably from Simport Plastics Limited (e.g., the T501 tubes).

Figure 21:
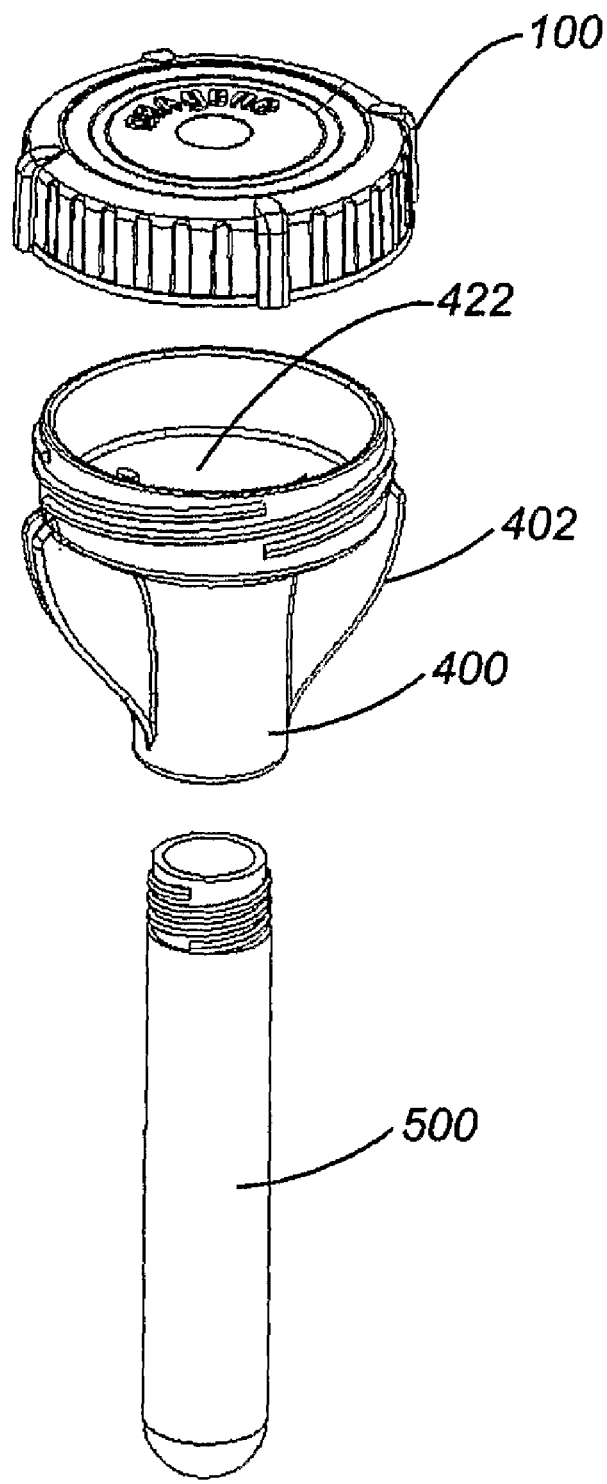
FIG. 21 is a side view of the container system depicted in FIG. 12, showing the lid, funnel, and vial separated.

The open end of vial 500 is also configured for securing attachment with a standard cap 520, as shown in FIG. 21. Cap 520 can be secured by a threaded screw, snap-fit, and the like.

Vial 500 optionally includes surface 502 that is suitable for labelling and/or for providing friction for gripping by a user.

Vial 500 may be removably attached to funnel 400 using a variety of locking mechanisms. In accordance with one embodiment of the present invention, the locking mechanism is a helical threaded screw. Alternatively, the locking mechanism is a snap-fit. Alternatively, vial 500 is fixedly attached to, or integral with, funnel 400.

In one example, lid 100 and funnel 400 are movable between an open position and a piercing position, as discussed supra with lid 100 and vial 1. In a specific example, lid 100 is initially attached to funnel 400 by threadingly engaging internal and external threads 108 and 18 with a twisting motion. Initially, lid 100 and funnel 400 are threadingly connected, but piercing member 6 does not disrupt pierceable membrane 160, and end portion 30 of wall 12 engages sealing wall 120. As depicted in FIGS. 9 and 16, sealing wall 120 extends downwardly and outwardly from the inner surface of lid 100. This type of sealing mechanism is similar to a wipe seal, that would be well known to the skilled worker. Thus, initially, interior channel 422 is maintained out of fluid communication with said reservoir 102 by pierceable membrane 6.

In an alternate example, lid 100 and funnel 400 are movable between a first position and a piercing position, as discussed supra with lid 100 and vial 1. Lid 100 is initially attached to funnel 400 by threadingly engaging internal and external threads 108 and 18 with a twisting motion. In moving lid 100 and funnel 400 to the first position, lid 100 and funnel 400 are threadingly connected, but piercing member 6 does not disrupt pierceable membrane 160. In the first position, end portion 30 of wall 12 sealingly engages sealing wall 120. As depicted in FIGS. 9 and 16, sealing wall 120 extends downwardly and outwardly from the inner surface of lid 100. This type of sealing mechanism is similar to a wipe seal, that would be well know to the skilled worker. Thus, in the first position, interior channel 422 is sealed against leakage to the outside of the container system and maintained out of fluid communication with said reservoir 102 by pierceable membrane 6.

Continued twisting moves lid 100 and funnel 400 from either the open position or the first position, to the piercing position, in which moving lid 100 and vial 1 together results in disruption of pierceable membrane 160 by piercing member 6, and the release of the substance within reservoir 102 into chamber 2 and vial 500.

In operation, in moving to the piercing position, pointed end 30 is brought into contact with pierceable membrane 160 and subsequently pierces pierceable membrane 160. Continued twisting moves cutting edge 32 through pierceable membrane 160, thereby disrupting pierceable membrane 160 and producing an opening in pierceable membrane 160 to permit the substance to enter interior channel 422. If more than one piercing member is present, less twisting of lid 100 and vial 1 is required to generate an opening. When three piercing members are present, a suitable opening is obtainable in about one quarter of a turn. Thus, in the piercing position, piercing member 6 disrupts pierceable membrane 160 to allow fluid communication between reservoir 102 and interior channel 422.

The distance between piercing member 6 and wall 104 will vary according to the needs and preferences of the user. The distance between piercing member 6 and wall 104 can vary from being generally flush with one another, to being generally separated from one another.

It will be clear to the skilled worker that length, rigidity and the like, of piercing member 6 is selected such that it sufficient to disrupt pierceable membrane 160 when lid 100 and vial 1 are in the piercing position, and not disrupt the pierceable membrane 160 when lid 100 and vial 1 are in the open or first position.

Methods

According to one embodiment of the present invention, the container system of the present application is suitable for releasably storing a composition intended to stabilize, preserve, or facilitate the recovery of nucleic acid from a biological sample. A biological sample can include bodily fluids and/or tissues.

Desirably, vial 1 and/or funnel 400 are sized for collecting a biological sample from a subject. Non-limiting examples of biological samples include skin, hair, fecal matter, bodily fluids, tissue, cells and the like.

The term "bodily fluid", as used herein, refers to a naturally occurring fluid from a human or an animal, such as saliva, sputum, serum, plasma, blood, pharyngeal, nasal/nasal pharyngeal and sinus secretions, urine, mucus, gastric juices, pancreatic juices, feces, semen, products of lactation or menstruation, tears, or lymph.

The term "bodily tissue" or "tissue", as used herein, refers to an aggregate of cells usually of a particular kind together with their intercellular substance that form one of the structural materials of a plant or an animal and that in animals include connective tissue, epithelium, muscle tissue, and nerve tissue, and the like.

The term "nucleic acid", as used herein, refers to a chain of nucleotides, including deoxyribonucleic acid (DNA) or ribonucleic acid (RNA), typically found in chromosomes, chromatin, mitochondria, ribosomes, cytoplasm, nucleus, microorganisms or viruses.

The term "ribonucleic acid" or "RNA", as used herein, refers to a wide range of RNA species, including, but not limited to high molecular RNA, large and small ribosomal RNAs, messenger RNA, pre-messenger RNA, small regulatory RNAs, RNA viruses (single and double-stranded, positive stranded or negative stranded) and the like. The RNA may be from a variety of sources, including, but not limited to human, non-human, viral, bacterial, fungal, protozoan, parasitic, single-celled, multi-cellular, in vitro, in vivo, natural, and/or synthetic sources.

Optionally the bodily fluid is saliva. The term "saliva", as used herein, refers to the secretion, or combination of secretions, from any of the salivary glands, including the parotid, submaxillary, and sublingual glands, optionally mixed with the secretions from the numerous small labial, buccal, and palatal glands that line the mouth.

The term "subject", as used herein, refers to an animal or human. Desirably, the subject is a mammal that can produce saliva for the purposes of nucleic acid stabilization and/or detection. Most desirably, the subject is human.

In use, a substance, such as a composition intended to stabilize, preserve, or facilitate the recovery of nucleic acid from a biological sample is sealed within reservoir 102 with a pierceable membrane. Suitable compositions include those described in International PCT application WO 2003/104251; International PCT application PCT/CA2006/000380; U.S. application Ser. Nos. 60/828,563; or 60/866,985, all of the contents of which are hereby incorporated by reference in their entirety. Desirably the composition is Oragene™ DNA-preserving solution. Other suitable compositions would be well known to the skilled worker.

In use, in one example, a sample of saliva from a subject is placed within chamber 2 of vial 1. Alternatively, vial 500 is attached to funnel 400, and a sample of saliva is placed within chamber 2 of funnel 400.

To collect saliva from a subject, in one example, the subject is instructed to wait for a period of 30-60 minutes before last eating. If possible, the subject will brush his teeth (without using toothpaste). If possible, the subject will rinse his/her mouth with 50 ml of water. The subject will be requested to wait for 5-10 minutes to allow the mouth to clear of water. For subjects able to spit, they will be instructed to spit saliva into the special collection vial until the level of saliva reaches the 1 or 2 ml mark. Waiting after last eating and rinsing the mouth is desirable but not essential. Collection of saliva may take several minutes. If the subject finds that he/she is unable to deliver sufficient saliva, he/she will be given a few grains of table sugar to chew, and told not to be concerned if some of the sugar is spit into the vial. For subjects unable to spit (e.g., infants, young children, individuals with limitations/disabilities), an implement (e.g., swab, transfer pipette) may be used for sample collection. Similarly, a subject may be provided a liquid (e.g., mouthwash, water, saline) to gargle his/her mouth and throat or saline to flush his/her nasal cavity. Samples collected with said liquid would be delivered into the collection vial.

A substance, such as a composition to stabilize, preserve, and/or facilitate the recovery of nucleic acid and saliva is stored within reservoir 102 of lid 100.

Lid 100 is then attached to vial 1, moved to the piercing position, and the substance combines with the saliva in chamber 2.

Alternatively, lid 100 is attached to funnel 400, moved to the piercing position, and the substance combines with the saliva in interior 530.

The combination of the composition to stabilize, preserve, or facilitate the recovery of nucleic acid and saliva may then be used in standard nucleic acid testing reactions, for example for detection or quantitation. Alternatively, the combination may be stored within container system 300 or 600 and subsequently used, for example, for detection of nucleic acid contained within the saliva. Alternatively, funnel 400 is removed from vial 500, and cap 520 is attached to the open end of vial 500. In this example, the combination may be stored within vial 500 and subsequently used, for example, for detection of nucleic acid contained within the saliva.

In one aspect of the present invention container system 300 and container system 600 are sized for shipping. In one example, vial 1 and lid 100 of container system 300 are sized for shipping when securely attached. In one example lid 1, funnel 400 and collection vial 500 of container system 600, are sized for shipping when lid 1, funnel 400 and collection vial 500 are securely attached. In another example, vial 1 and lid 100 of container system 300 are sized for shipping when vial 1 and lid 100 are separate. In another example, lid 1, funnel 400 and collection vial 500 of container system 600, are sized for shipping when lid 1, funnel 400 and collection vial 500 are separate. It will be appreciated that a variety methods of shipping are contemplated. Non-limiting examples of shipping include shipping by hand, land, air, boat, animal, and the like, or combinations thereof. Desirably, container system 300 or container system 600 fit within a standard mail envelope. In one example, container system 300 or container system 600 fit within an envelope sized to fit within a standard European mail slot. In a specific example, the standard European mail slot has a width of about 3 cm. Alternatively, container system 300 or container system 600 fit within an envelope sized to fit within a standard Canadian and/or United States of America mail slot.

Another aspect of the present invention provides a method of manufacture of a device for releasably storing a substance. The method of manufacture comprises providing container system in accordance with the present invention.

Another aspect of the present invention provides a method of combining a substance with a biological sample. This method comprises providing a container system in accordance with the present invention, wherein the container system includes the substance, and providing the biological sample.

Another aspect of the present invention provides a method of preserving nucleic acid in a biological sample. This method comprises providing a container system in accordance with the present invention, wherein the container system includes a substance for preserving nucleic acid in a biological sample.

Another aspect of the present invention provides a method of archiving a biological sample for prolonged periods of time. Desirably archiving is at room temperature. This method comprises providing a container system in accordance with the present invention and providing a substance for archiving the biological sample. In one example, prolonged storage is at room temperature for more than about one week, about two weeks, about three weeks, about one month, more than about one month, about one year.

Kit

Another aspect of the present invention provides a kit for collection of a sample and mixing the sample with a substance. The kit includes a container system in accordance with the present invention and instructions for the use thereof, optionally with a substance stored within the lid of the container system.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A container system for releasably storing a substance, comprising:
   a) a vial comprising a first open end for receiving a sample, a second end comprising a sample storage chamber and a piercing member, wherein said piercing member comprises a side wall, a first cutting edge extending from a first pointed corner to a second corner that defines the intersection between said cutting edge and said side wall; and b) a lid configured to removably engage said vial, said lid comprising a reservoir for holding the substance, and a pierceable membrane sealing the substance within said reservoir, wherein, when said system is closed by removable engagement of said vial with said lid, said vial and said lid are movable to a piercing position in which the piercing member disrupts the pierceable membrane to allow fluid communication between said reservoir and said chamber, wherein the chamber is sealed against leakage to the outside of the container system in the piercing position.

2. The container system of claim 1 wherein said lid comprises a wall defining all or a portion of the perimeter of said reservoir, said wall having a sealing surface for sealingly attaching said pierceable membrane.

3. The container system of claim 1, wherein said reservoir is configured to retain about 1 ml to about 4 ml of said substance.

4. The container system of claim 1, wherein said pierceable membrane is inert.

5. The container system of claim 1, wherein said pierceable membrane remains intact and pierceable at temperatures of from about −80° C. to about 70° C.

6. The container system of claim 1, wherein said pierceable membrane is sealingly attached to said sealing surface by an adhesive, a heat-sealing treatment, a fastener, or any combinations thereof.

7. The container system of claim 1, wherein the width of said first end is equivalent to the width of said second end.

8. The container system of claim 1, wherein said first end is generally wider than said second end.

9. The container system of claim 1, wherein said chamber is configured to receive about 1 ml to about 16 ml of said sample.

10. The container system of claim 9, wherein said chamber is configured to receive about 1 ml to about 4 ml of said sample.

11. The container system of claim 1, wherein the said piercing member extends from a base surface of said chamber.

12. The container system of claim 11, wherein said piercing member extends approximately perpendicularly from said base.

13. The container system of claim 11, wherein said piercing member is angled inwardly or outwardly toward said first open end of said vial.

14. The container system of claim 1, wherein said side wall further includes a second cutting edge.

15. The container system of claim 1, wherein said vial comprises a plurality of piercing members.

16. The container system of claim 15, wherein said vial comprises three piercing members.

17. The container system of claim 15, wherein said vial comprises two piercing members.

18. The container system of claim 1, wherein said system comprises sealing means for sealing said chamber against leakage to the outside of said container system following movement of said container system to said piercing position.

19. The container system of claim 18, wherein said sealing means comprises a sealing wall about the interior circumference of said lid that sealingly engages a surface of said vial when the system is in said piercing position.

20. The container system of claim 1, wherein said vial and said lid are sized for shipping in both an unattached state and an attached state.

21. A container system for releasably storing a substance, comprising:

a) a vial comprising a chamber for retaining a sample b) a lid comprising a reservoir for holding the substance, and a pierceable membrane sealing the substance within said reservoir; and c) a funnel comprising a first open end for receiving said sample, a piercing member and a channel extending from said first open end to a second open end and being in fluid communication with said chamber, said funnel being removably attachable to said lid at said first open end and releasably or permanently attached to said vial at said second end, wherein said piercing member comprises a side wall, and a first cutting edge extending from a first pointed corner to a second corner that defines the intersection between said cutting edge and said side wall;

wherein, when said system is closed by removable attachment of said lid to said funnel, said system is movable to a piercing position in which the piercing member disrupts the pierceable membrane to allow fluid communication between said reservoir and said chamber, via said channel, wherein the chamber is sealed against leakage to the outside of the container system in the piercing position.

22. The container system of claim 21 wherein said lid comprises a wall defining all or a portion of the perimeter of said reservoir and including a sealing surface for sealingly attaching said pierceable membrane.

23. The container system of claim 21, wherein said reservoir is configured to retain about 1 ml to about 4 ml of said substance.

24. The container system of claim 21 wherein said pierceable membrane is inert.

25. The container system claim 21, wherein said pierceable membrane maintains intact and pierceable at temperatures of from about −80° C. to about 70° C.

26. The container system of claim 21, wherein said pierceable membrane is sealingly attached to said sealing surface by an adhesive, a heat-sealing treatment, a fastener, or any combinations thereof.

27. The container system of claim 21, wherein said piercing member extends from an interior surface of said funnel.

28. The container system of claim 27, wherein said piercing member is angled inwardly or outwardly toward said first open end of said funnel.

29. The container system of claim 21, wherein said side wall includes a second cutting edge.

30. The container system of claim 21, wherein said funnel comprises a plurality of piercing members.

31. The container system of claim 30, wherein said funnel comprises three piercing members.

32. The container system of claim 31, wherein said funnel comprises two piercing members.

33. The container system of claim 21, wherein said system comprises sealing means for sealing said chamber against leakage to the outside of said container system.

34. The container system of claim 33, wherein said sealing means comprises a sealing wall about the interior circumference of said lid that sealingly engages a surface of said funnel when the system is in the piercing position.

35. The container system of claim 21, wherein said vial is releasably attached to said funnel and sized for attachment to a cap when released from said funnel.

36. The container system of claim 21, wherein said vial is configured for use in standard laboratory equipment.

37. The container system of claim 36, wherein said vial is a T501 tube.

38. The container system of claim 21, wherein said chamber is sized to hold about 1 ml to about 16 ml.

39. The container system of claim 1 or 21, wherein said substance is a composition for the stabilization and recovery of a nucleic acid from a biological sample.

40. The container system of claim 39, wherein said nucleic acid is DNA or RNA.

41. A method of combining a substance with a biological sample, comprising:
   (a) providing the container system of claim 1;
   (b) providing the sample to the chamber in the vial; and
   (c) closing said container system by removably attaching said lid to said vial; and
   (d) piercing said membrane to release said substance into said chamber by moving said lid and said vial to said piercing position.

42. A method of combining a substance with a biological sample, comprising:
   (a) providing the container system of claim 21;
   (b) providing the sample to the chamber in the vial through said funnel; and
   (c) closing said container system by removably attaching said lid to said first open end of said funnel; and
   (d) piercing said membrane to release said substance into said chamber by moving said system to said piercing position.

43. The method of claim 41 or 42, wherein the substance is a nucleic acid preserving substance.

44. The method of claim 41 or 42, wherein the sample is a biological sample.

45. The method of claim 41 or 42, for archiving the sample.

46. A kit for sample collection and storage, comprising:
   a) a container system of claim 1 or 21; and
   b) instructions for the use thereof.

47. The container system of claim 1, wherein the substance is a liquid.

48. The container system of claim 21, wherein the substance is a liquid.

49. The container system of claim 1, additionally comprising a solid or semi-solid material within said vial and maintained separate from the substance in the reservoir of said lid until said pierceable membrane is disrupted.

50. The container system of claim 21, additionally comprising a solid or semi-solid material within said vial and maintained separate from the substance in the reservoir of said lid until said pierceable membrane is disrupted.

\* \* \* \* \*